US012673186B2

(12) United States Patent
Staley et al.

(10) Patent No.: US 12,673,186 B2
(45) Date of Patent: Jul. 7, 2026

(54) CATHETER TIP PASSIVE CONTROL DEVICE AND RELATED SYSTEMS AND METHODS

(71) Applicant: Becton, Dickinson and Company, Franklin Lakes, NJ (US)

(72) Inventors: Shaun Staley, Murray, UT (US); Megan Scherich, Salt Lake City, UT (US); Jonathan Karl Burkholz, Salt Lake City, UT (US); Yiping Ma, Layton, UT (US); Yueqiang Xue, Shanghai (CN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1056 days.

(21) Appl. No.: 17/346,044

(22) Filed: Jun. 11, 2021

(65) Prior Publication Data

US 2021/0402156 A1 Dec. 30, 2021

Related U.S. Application Data

(60) Provisional application No. 63/046,291, filed on Jun. 30, 2020.

(51) Int. Cl.
A61M 25/09 (2006.01)
A61M 25/00 (2006.01)
A61M 25/01 (2006.01)

(52) U.S. Cl.
CPC ........ A61M 25/09 (2013.01); A61M 25/0026 (2013.01); A61M 25/0158 (2013.01);
(Continued)

(58) Field of Classification Search
CPC ......... A61M 2025/09158; A61M 2025/09141; A61M 2025/0064; A61M 25/0158; A61M 25/0152; A61M 25/0606
See application file for complete search history.

(56) References Cited

U.S. PATENT DOCUMENTS

| 5,019,040 A | * | 5/1991 | Itaoka | A61B 18/26 604/20 |
| 5,055,101 A | * | 10/1991 | McCoy | H01H 37/323 604/528 |

(Continued)

FOREIGN PATENT DOCUMENTS

| DE | 102018203102 B3 | * | 5/2019 | A61B 5/055 |
| EP | 3449965 A1 | * | 3/2019 | A61M 25/0043 |

(Continued)

OTHER PUBLICATIONS

Burkholz, et al., Tubular Instrument and Related Devices and Methods, U.S. Appl. No. 17/143,095, filed Jan. 6, 2021.

*Primary Examiner* — Bhisma Mehta
*Assistant Examiner* — Adam J. Cermak
(74) *Attorney, Agent, or Firm* — The Webb Law Firm

(57) ABSTRACT

A vascular access device to passively open a fluid path within a vasculature. The vascular access device may include a catheter and a guidewire. The catheter may have a proximal end, a tip, and a length of tubing therebetween. The guidewire may extend along the length of tubing and may include a bent portion. At least a portion of the length of tubing may substantially conform to the bent portion such that the tip of the catheter avoids an obstruction within the vasculature.

11 Claims, 6 Drawing Sheets

(52) U.S. Cl.
CPC .............. *A61M 2025/0186* (2013.01); *A61M 2025/09141* (2013.01); *A61M 2205/0266* (2013.01)

(56) References Cited

U.S. PATENT DOCUMENTS

| | | | | |
|---|---|---|---|---|
| 5,257,974 A * | 11/1993 | Cox .................... | A61M 25/104 604/103.05 |
| 5,279,559 A * | 1/1994 | Barr .................. | A61M 25/0158 604/95.05 |
| 5,357,979 A * | 10/1994 | Imran .............. | A61M 25/0158 604/95.05 |
| 5,383,923 A * | 1/1995 | Webster, Jr. ......... | A61B 5/6855 607/125 |
| 5,762,630 A * | 6/1998 | Bley ........................ | A61L 29/14 604/524 |
| 5,820,592 A * | 10/1998 | Hammerslag ..... | A61M 25/0152 604/95.01 |
| 5,846,247 A * | 12/1998 | Unsworth ......... | A61M 25/0043 606/198 |
| 5,904,657 A * | 5/1999 | Unsworth ......... | A61M 25/0155 600/585 |
| 5,931,819 A * | 8/1999 | Fariabi .............. | A61M 25/0158 604/525 |
| 6,083,170 A * | 7/2000 | Ben-Haim ............... | A61B 8/06 600/463 |
| 6,096,036 A * | 8/2000 | Bowe .................... | B82Y 15/00 606/41 |
| 6,652,491 B1 * | 11/2003 | Walker .............. | A61M 25/0102 604/164.01 |
| 6,749,628 B1 * | 6/2004 | Callol .................... | A61F 2/954 623/1.35 |
| 7,914,503 B2 * | 3/2011 | Goodson, IV ........ | A61M 25/04 604/264 |
| 8,118,803 B1 * | 2/2012 | Chow .............. | A61M 25/0152 604/524 |
| 10,806,898 B2 * | 10/2020 | Konh .................... | A61F 2/2466 |
| 10,898,678 B2 * | 1/2021 | Walzman .......... | A61M 25/0662 |
| 11,324,931 B2 * | 5/2022 | Marsman .............. | A61M 25/09 |
| 12,458,423 B2 * | 11/2025 | Rupp ................. | A61B 18/1206 |
| 2001/0039412 A1 * | 11/2001 | Fariabi .................. | A61M 25/09 604/170.03 |
| 2002/0142119 A1 * | 10/2002 | Seward ................. | A61L 29/126 428/371 |
| 2003/0181855 A1 * | 9/2003 | Simpson ........... | A61M 25/0041 604/95.04 |
| 2004/0002683 A1 * | 1/2004 | Nicholson ............. | A61M 25/01 604/164.01 |
| 2004/0186378 A1 * | 9/2004 | Gesswein ......... | A61M 25/0152 604/528 |
| 2005/0070844 A1 * | 3/2005 | Chow .............. | A61M 25/0147 604/95.04 |
| 2006/0036218 A1 * | 2/2006 | Goodson .............. | A61M 25/04 604/264 |
| 2006/0064055 A1 * | 3/2006 | Pile-Spellman .. | A61M 25/0105 604/95.05 |
| 2007/0270679 A1 * | 11/2007 | Nguyen ............ | A61M 25/0043 600/585 |
| 2007/0270781 A1 * | 11/2007 | Burgermeister .......... | A61F 2/95 604/528 |
| 2008/0009831 A1 * | 1/2008 | Griffin .............. | A61M 25/0054 604/113 |
| 2008/0077049 A1 * | 3/2008 | Hirshman ............. | A61M 25/09 600/585 |
| 2009/0131948 A1 * | 5/2009 | Liu ................... | A61M 25/0152 606/92 |
| 2010/0152663 A1 * | 6/2010 | Darr .................. | A61M 25/0152 604/164.01 |
| 2010/0168666 A1 * | 7/2010 | Tegg ................. | A61M 25/0147 604/95.04 |
| 2010/0203234 A1 * | 8/2010 | Anderson ............... | A61L 29/02 83/875 |
| 2012/0323174 A1 * | 12/2012 | Shih .................. | A61M 25/0158 604/95.04 |
| 2014/0088560 A1 * | 3/2014 | Min ...................... | A61L 29/085 604/528 |
| 2014/0276619 A1 * | 9/2014 | Deshpande ....... | A61M 25/0021 604/528 |
| 2015/0099936 A1 * | 4/2015 | Burdulis ........... | A61N 1/36071 604/523 |
| 2015/0112304 A1 * | 4/2015 | Silvestro .......... | A61M 25/0194 604/170.03 |
| 2015/0282693 A1 * | 10/2015 | Hakkens .............. | A61B 1/0011 604/95.05 |
| 2015/0343176 A1 * | 12/2015 | Asleson ............ | A61B 17/3468 606/129 |
| 2016/0175039 A1 * | 6/2016 | Aujla ................. | A61M 25/0009 72/364 |
| 2016/0220741 A1 * | 8/2016 | Garrison .......... | A61M 25/0054 |
| 2016/0317788 A1 * | 11/2016 | Merkel ............. | A61M 25/0068 |
| 2017/0333237 A1 * | 11/2017 | Walzman .......... | A61M 25/1011 |
| 2018/0132837 A1 * | 5/2018 | Mathena ............. | A61M 39/227 |
| 2018/0296731 A1 * | 10/2018 | Lim ................... | C08G 18/6674 |
| 2019/0262589 A1 * | 8/2019 | Marsman .......... | A61M 25/0041 |
| 2019/0282266 A1 * | 9/2019 | Walzman .......... | A61M 25/0105 |
| 2019/0374746 A1 * | 12/2019 | Konh ...................... | A61B 34/30 |
| 2020/0238053 A1 * | 7/2020 | Lee ................... | A61M 25/0127 |
| 2020/0376237 A1 * | 12/2020 | Hayakawa ........... | A61M 25/09 |
| 2021/0023339 A1 * | 1/2021 | Hayes ............... | A61B 1/00078 |
| 2021/0106791 A1 * | 4/2021 | Uihlein ............. | A61M 25/0127 |
| 2021/0220605 A1 * | 7/2021 | Burkholz .......... | A61M 25/0043 |
| 2021/0282759 A1 * | 9/2021 | Layman ................ | A61M 25/09 |
| 2021/0353130 A1 * | 11/2021 | Cazeneuve ......... | A61B 1/0055 |
| 2022/0361946 A1 * | 11/2022 | Smith ............... | A61M 25/0102 |
| 2025/0178189 A1 * | 6/2025 | Cazeneuve ....... | A61M 25/0158 |

FOREIGN PATENT DOCUMENTS

| | | | | |
|---|---|---|---|---|
| JP | 20019041 A | 1/2001 | | |
| WO | 9837923 A2 | 9/1998 | | |
| WO | 9956810 A1 | 11/1999 | | |
| WO | WO-2007022383 A2 * | 2/2007 | ............ | A61M 25/01 |
| WO | WO-2012043178 A1 * | 4/2012 | ......... | A61B 1/00006 |

* cited by examiner

CATHETER TIP PASSIVE CONTROL DEVICE AND RELATED SYSTEMS AND METHODS

BACKGROUND

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient to obtain a blood sample.

A common type of catheter is an over-the-needle peripheral intravenous ("IV") catheter. As its name implies, the over-the-needle catheter may be mounted over an introducer needle having a sharp distal tip. The catheter and the introducer needle may be assembled so that the distal tip of the introducer needle extends beyond the distal tip of the catheter with the bevel of the needle facing up away from skin of the patient. The catheter and introducer needle are generally inserted at a shallow angle through the skin into vasculature of the patient.

In order to verify proper placement of the introducer needle and/or the catheter in the blood vessel, a clinician generally confirms that there is "flashback" of blood in a flashback chamber of the catheter assembly. Once placement of the needle has been confirmed, the clinician may temporarily occlude flow in the vasculature and remove the needle, leaving the catheter in place for future blood withdrawal, fluid infusion, or probe access.

Catheter functionality, however, may be impeded for several reasons, particularly when there is a prolonged dwelling time of the catheter within the vasculature. More generally, over time, catheters may become susceptible to complications and obstructions that impede fluid flow. For example, a catheter may become occluded at its tip due to the presence of fibrin sheath, thrombus, vein walls, or valves. As a result, while catheters are commonly used for acquiring a blood sample at a time of catheter placement, they are less commonly used for acquiring a blood sample during the catheter dwell period. When a blood sample is desired during the catheter dwell period, an additional needle stick is typically used to provide vein access for blood collection, causing additional pain for the patient as well as increased material costs. It has been shown, however, that applying traction to move or re-position the catheter tip within the vein may improve blood draw success and catheter functionality significantly by avoiding occlusions and obstacles.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to vascular access devices or intravenous catheters to infuse fluids and/or collect blood from the vasculature of a patient. Various complications and obstructions may impede fluid flow through the catheter, however, thus compromising catheter functionality for infusion and/or aspiration. For example, the catheter may become occluded at its tip due to the presence of fibrin sheath, thrombus, vein walls, or valves. Re-positioning the catheter tip within the patient's vasculature to open a fluid path may significantly improve catheter functionality and blood draw success.

Some embodiments herein disclose a vascular access device that enables aspirations, blood draws, and infusions by passively repositioning the tip of the catheter and opening a fluid path. In some embodiments, a vascular access device to passively open a fluid path within a vasculature may include a catheter and a guidewire. In some embodiments, the catheter may include a proximal end, a tip, and a length of tubing therebetween. In some embodiments, a guidewire may extend along the length of tubing and may include a bent portion. In some embodiments, at least a portion of the length of tubing may substantially conform to the bent portion within the vasculature such that the tip of the catheter may avoid an obstruction therein.

In some embodiments, the guidewire may be coupled to at least a portion of a surface of the catheter. Alternatively, in some embodiments, the guidewire may be embedded into at least a portion of the catheter. Some embodiments of the catheter may include one or more fenestrations disposed therein to provide additional fluid paths.

In some embodiments, the guidewire may include a temperature-activated material, such as nitinol or scandium trifluoride ($ScF_3$). In some embodiments, the catheter and the guidewire may include unique thermal expansion characteristics. In some embodiments, the guidewire may be oriented along the length of tubing such that the tip of the catheter is directed upwards, downwards, or laterally with respect to a longitudinal axis of the vasculature.

Some embodiments may include a catheter assembly to passively open a fluid path. In some embodiments, the catheter assembly may include a catheter adapter having a proximal end, a distal end, and a lumen extending therebetween. In some embodiments, the catheter may extend from the distal end of the catheter adapter. In some embodiments, the catheter may include the tip and the length of tubing. In some embodiments, the length of tubing may include the resilient bent portion. Some embodiments of the resilient bent portion may include an initial shape where a first portion of the length of tubing is misaligned with respect to a second portion of the length of tubing.

Some embodiments of the catheter assembly may further include a needle configured to extend through the length of tubing. In some embodiments, the resilient bent portion and the tip of the catheter may conform to the needle in response to the needle extending therethrough. In some embodiments, in response to the needle being withdrawn in a proximal direction, the resilient bent portion may return to the initial shape such that the tip of the catheter misaligns with the length of the tubing within the vasculature.

In some embodiments, the resilient bent portion may include an asymmetrical cross-section, an extended length, and/or one or more joints. In some embodiments, the catheter may include a guidewire extending along the length of tubing. In some embodiments, the guidewire may be coupled to at least a portion of the surface of the catheter. In some embodiments, the guidewire may be embedded into at least a portion of a wall of the catheter.

In some embodiments, the resilient bent portion may direct the tip of the catheter upward relative to a longitudinal axis of the vasculature. In some embodiments, the resilient bent portion may direct the tip of the catheter downward relative to the longitudinal axis. In some embodiments, the resilient bent portion may direct the tip of the catheter laterally relative to the longitudinal axis.

In some embodiments, the catheter assembly to passively open a fluid path may include the catheter and a thermal element. In some embodiments, the catheter may include a proximal end, a tip, and a length of tubing therebetween. In some embodiments, the thermal element may be coupled to the length of tubing. Some embodiments of the thermal element may be temperature-activated to change shape in response to being disposed within the vasculature. In some embodiments, the catheter and the thermal element may be monolithically formed as a single unit.

It is to be understood that both the foregoing general description and the following detailed description are examples and explanatory and are not restrictive of the invention, as claimed. It should be understood that the various embodiments are not limited to the arrangements and instrumentality illustrated in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL
VIEWS OF THE DRAWINGS

Example embodiments will be described and explained with additional specificity and detail through the use of the accompanying drawings in which.

4

Figure 9A:
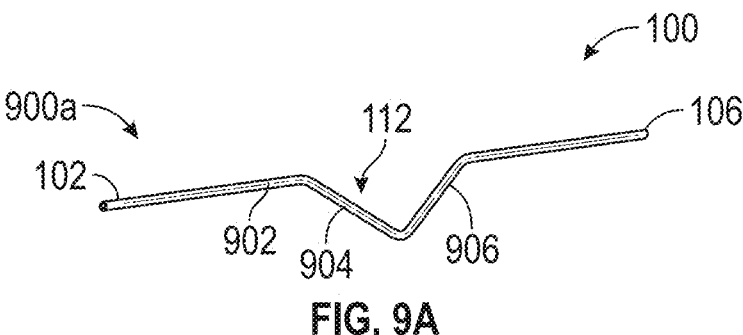
FIG. 9A is a perspective view of an example guidewire having an example bent portion according to some embodiments.
Figure 9B:
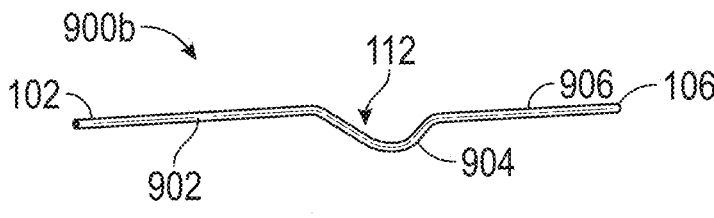
FIG. 9B is a perspective view of another example guidewire having another example bent portion according to some embodiments.
Figure 9C:
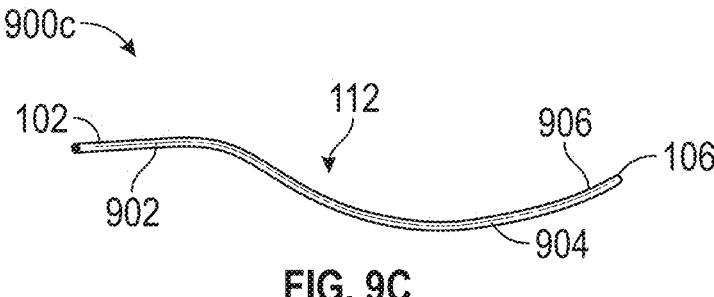
FIG. 9C is a perspective view of another example guidewire having another example bent portion according to some embodiments.
Figure 9D:
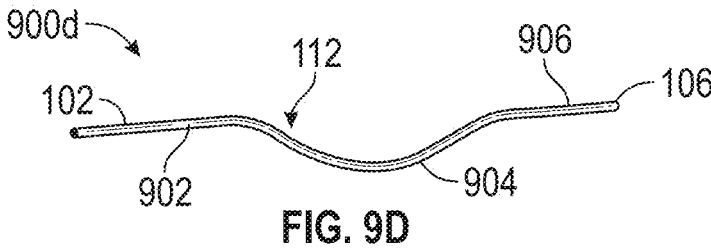
Figure 9E:
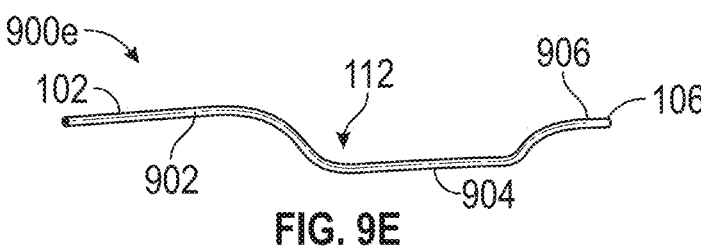

FIG. 9D is a perspective view of another example guidewire having another example bent portion according to some embodiments; and FIG. 9E is a perspective view of another example guidewire having another example bent portion according to some embodiments.

DETAILED DESCRIPTION

As used in this specification, the term "distal" refers to a direction away from a clinician who would place the device into contact with a patient, and nearer to the patient. The term "proximal" refers to a direction nearer to the clinician who would place the device into contact with the patient, and farther away from the patient. Thus, for example, the end of a catheter first touching the body of the patient is the distal end, while the opposite end of the catheter is the proximal end of the catheter.

As previously mentioned, catheter functionality may be impeded for several reasons, particularly when a dwelling time of a catheter within a vasculature is prolonged. For example, the catheter may become occluded at its tip due to the presence of fibrin sheath, thrombus, vein walls, or valves. Particularly, the catheter tends to form an "S" shape when placed within a vein, causing the tip of the catheter to rest against an opposite vein wall. Such close proximity between the vein wall and the catheter may encourage relative motion between the two, leading to formation of thrombus on the vein wall and/or catheter tip. In addition, the close proximity of the catheter tip to the vein wall may lead to stasis near the catheter tip, thereby promoting thrombus formation.

Applying traction to move or re-position the catheter tip within the vein may significantly improve blood draw success and catheter functionality by avoiding such occlusions and obstacles. Embodiments described herein may enable aspirations, blood draws, and/or infusions by passively repositioning the tip of the catheter within the vasculature away from the vein wall to minimize the likelihood of thrombus formation near the catheter tip and thereby extending the patency of a fluid path.

Figure 1:
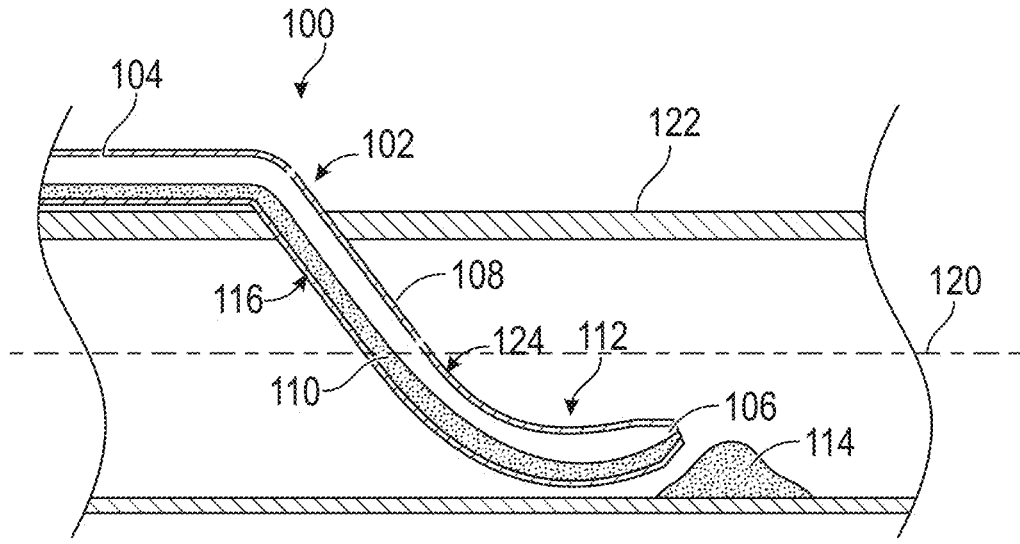
FIG. 1 is a cross-sectional view of an example vascular access device, illustrating an example catheter having a pre-shaped guidewire according to some embodiments.

Referring now to FIG. 1, in some embodiments, a vascular access device 100 may be configured to passively control a location of a tip 106 of a catheter 102 within a patient's vasculature 122 to avoid obstructions and open a fluid path for blood collection or fluid delivery. In some embodiments, the catheter 102 may include a peripheral IV catheter 102, a peripherally-inserted central catheter 102, or a midline catheter 102. In some embodiments, the catheter 102 may have been previously inserted into the vasculature 122 of a patient and may be dwelling within the vasculature 122. In such cases, the catheter 102 may be susceptible to blockage by debris (e.g., fibrin or platelet clots), and/or adhering of the tip 106 of the catheter 102 to the vasculature 122. Thus, blood withdrawal using the catheter 102 may be particularly difficult.

Some embodiments herein disclose a vascular access device 100 that facilitates aspirations, blood draws, and/or infusions by passively repositioning the tip 106 of the catheter 102 within the vasculature 122 to open a fluid path. As shown in FIG. 1, in some embodiments, the vascular access device 100 to passively open the fluid path within the vasculature 122 may include a catheter 102 and one or more guidewires 110. In some embodiments, the catheter 102 may include a proximal end 104, a tip 106, and a length of tubing 108 defining a lumen therebetween.

In some embodiments, the guidewire 110 may be embedded into at least a portion of the catheter 102. Some embodiments of the guidewire 110 may be coextruded in the catheter 102 such that the guidewire 110 extends partially or fully along the length of tubing 108. In other embodiments, the guidewire 110 may be coupled to at least a portion of an outer or inner surface 116, 124 of the catheter 102. In some embodiments, the guidewire 110 may prevent kinking of the catheter 102 at the insertion site, for example.

Figure 5:
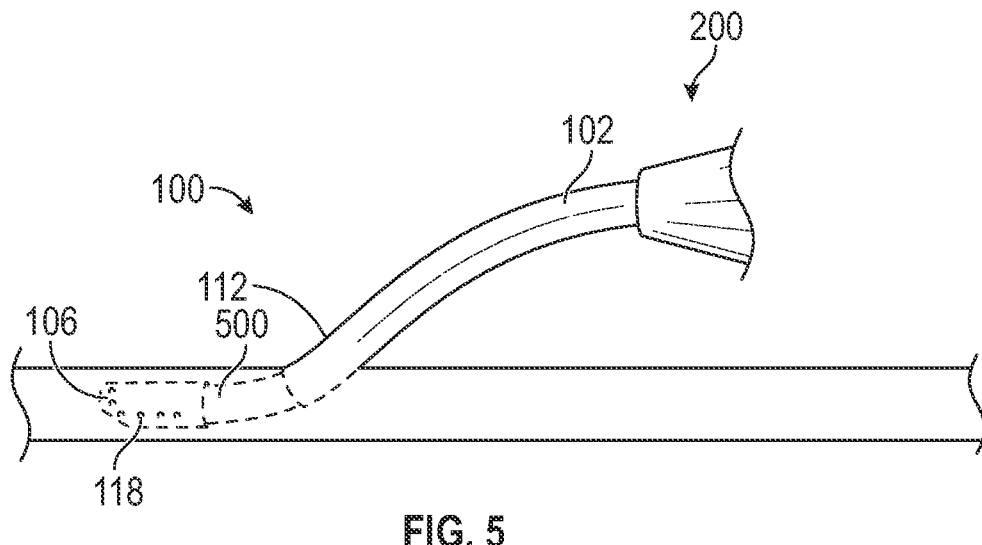
FIG. 5 is a side perspective view of another example vascular access device comprising a jointed catheter disposed within a vasculature according to some embodiments.

In some embodiments, the catheter 102 may include one or more fenestrations 118 to provide additional fluid paths. In some embodiments, as shown in FIG. 5, the fenestrations 118 may be disposed along the length of tubing 108 and/or at the tip 106 of the catheter 102.

In some embodiments, the guidewire 110 may include a bent portion 112. In some embodiments, the guidewire 110 may include a resilient or shape memory wire or other suitable material having a unique pre-formed shape. In some embodiments, the guidewire 110 may be pre-formed into a curve or another suitable non-linear shape. In some embodiments, the guidewire 110 may be pre-formed via heat shaping, mechanical shaping, or another suitable shaping technique.

In some embodiments, the guidewire 110 may include a metal, metal alloy, polycarbonate, plastic, or other suitable material. In some embodiments, at least a portion of the length of tubing 108 may substantially conform to the bent portion 112 of the guidewire 110 within the vasculature 122. In this manner, the tip 106 of the catheter 102 may be passively directed away from any blockage or obstruction 114 within the vasculature 122.

Figure 2:
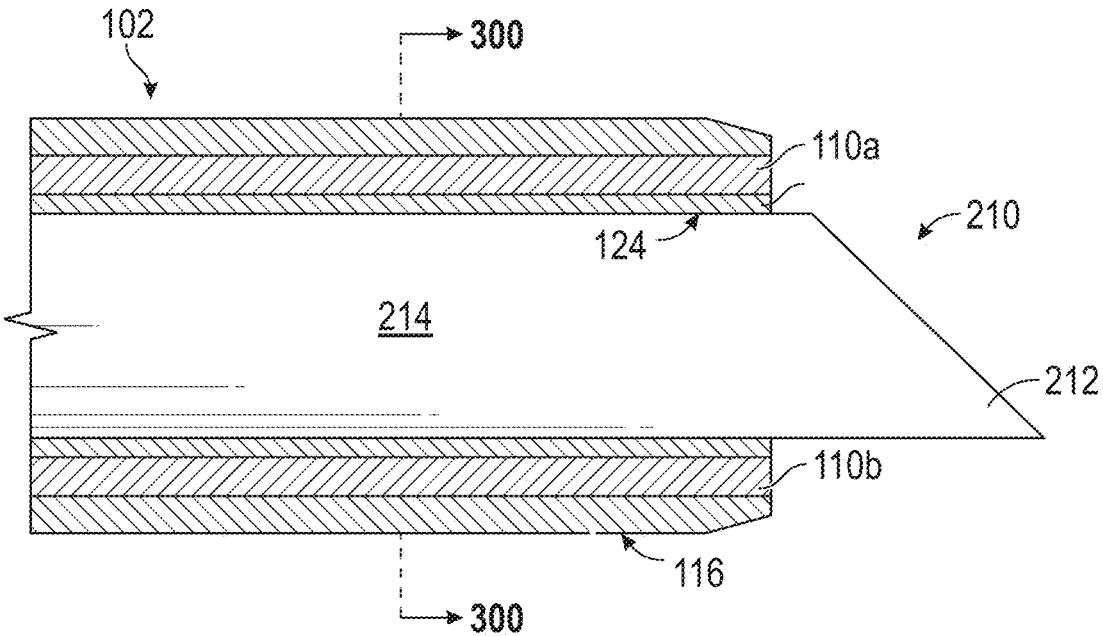
FIG. 2 is a cross-sectional view of another example vascular access device, illustrating an example needle extending therethrough according to some embodiments.

Referring now to FIG. 2, in some embodiments, the catheter 102 may be configured to receive a needle 210 having a lumen 214 and a sharp distal tip 212, where the needle 210 extends through the length of the catheter 102. In some embodiments, the sharp distal tip 212 of the needle 210 may be exposed at the tip 206 of the catheter 102 to introduce the catheter 102 to the vasculature 122.

In some embodiments, the catheter 102 may conform to the shape of the guidewire 110, including the bent portion 112. In some embodiments, at least a portion of the catheter 102, including the bent portion 112, may conform to the shape of the needle 210 as the needle 210 extends therethrough. For example, in some embodiments, the bent portion 112 of the catheter 102 and/or guidewire 110 may be straightened as the needle 210 is inserted into the catheter 102 and advanced in a distal direction therethrough.

In some embodiments, upon removal of the needle 210 from the catheter 102, the bent portion 112 may return to its initial shape. Some embodiments of the catheter 102 may then conform to the pre-formed shape of the guidewire 110 and bent portion 112. In some embodiments, the bent portion 112 of the guidewire 110 may include one or more bends. For example, in some embodiments, the bent portion 112 may include a bend at or proximate the tip 106. In some embodiments, the bent portion 112 may provide one or more bends more proximally along the length of tubing 108. In one embodiment, for example, the bent portion 112 may include multiple bends to provide an "s" curve shape along the length of tubing 108.

In this manner, some embodiments of the catheter 102 passively move the tip 106 of the catheter 102 such that the tip 106 of the catheter 102 misaligns with the length of the tubing 108 within the vasculature 122. In some embodiments, the pre-formed shape of the guidewire 110 may lift the tip 106 of the catheter 102 toward the center of the vasculature 122. In this manner, the tip 106 of the catheter 102 may be directed away from an obstruction 114 on the vein periphery such as thrombus, for example.

In some embodiments, the guidewire 110 may include a strip of material coupled to an exterior surface of the catheter 102. In other embodiments, the guidewire 110 may be extruded in stripe with the catheter 102. Some embodiments of the guidewire 110 may be configured to bend in response to being disposed within the vasculature 122. For example, as discussed in more detail below, in some embodiments the guidewire 110 may be configured to bend in response to the increased temperature of the vasculature 122. In some embodiments, such bending may lift the tip 106 away from the wall, ceiling or floor of the vasculature 122 when the needle 210 is removed from the catheter 102.

In some embodiments, the guidewire 110 may include a thermal element or any suitable temperature-activated material. In some embodiments, the temperature-activated material may include a strip of pre-formed or other shape-memory metal or plastic configured to return to its pre-formed shape upon the needle 210 being removed from the catheter 102. In some embodiments, the catheter 102 and the guidewire 110 may include unique thermal expansion characteristics. For example, in some embodiments, the guidewire 110 may include scandium trifluoride ($SCF_3$) or another such material that may contract with increasing temperature. In some embodiments, the scandium trifluoride or other suitable material may be located on the top section of the catheter 102 tubing along its circumference. In this manner, in some embodiments, contraction of the material may lift the catheter tip 106 away from the vein wall. In other embodiments, the guidewire 110 may include nitinol or other similar or suitable material.

Figure 3:
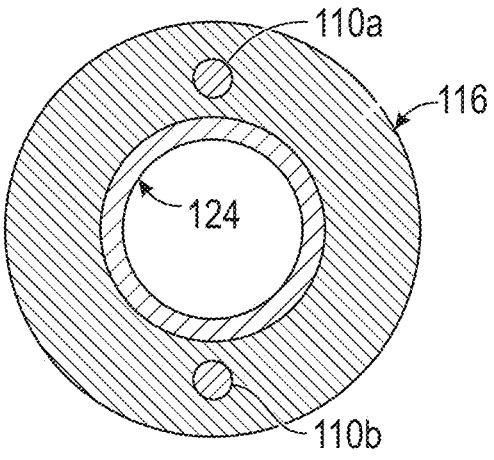
FIG. 3 is a cross-sectional view of the vascular access device of FIG. 2, where the cross-section is taken along the illustrated line.

In some embodiments, more than one guidewire 110 may be embedded into or coupled to the catheter 102. As shown in FIGS. 2 and 3, in some embodiments, multiple guidewires 110a, 110b may be embedded into opposite sides of the outer surface 116 of the catheter 102. In some embodiments, the multiple guidewires 110 may be similarly shaped to increase a force applied to re-configure a shape of the catheter 102 upon removing the needle 210.

In some embodiments, one or more guidewires 110 may be oriented along the length of tubing 108 such that the tip 106 of the catheter 102 may be directed upwards, downwards, or laterally with respect to a longitudinal axis 120 of the vasculature 122. In some embodiments, one or more guidewires 110 may be similarly or uniquely oriented with respect to one or more other guidewires 110 along the length of tubing 108. FIG. 3 illustrates a cross-section of the catheter 102 and guidewires 110 of FIG. 2 taken along the line 300. As shown, multiple guidewires 110a, 110b may be evenly spaced with respect to the catheter wall. In other embodiments, the multiple guidewires 110a, 110b may be grouped together or otherwise located or oriented as desired to promote passive bending of the length of tubing 108 and/or creation of the bent portion 112.

Figure 4:
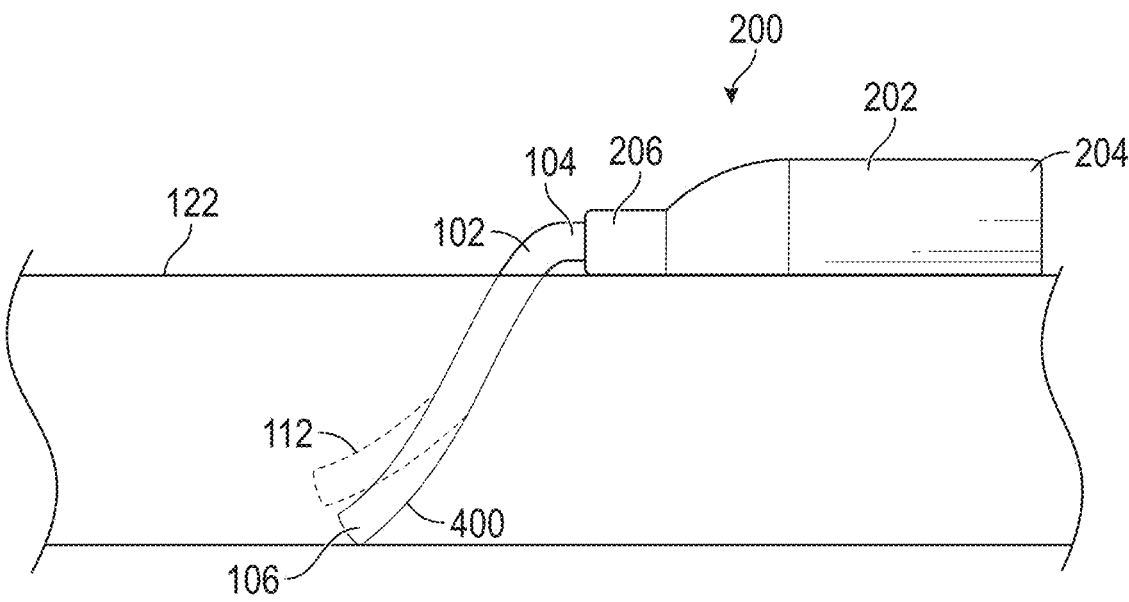
FIG. 4 is a side perspective view of an example vascular access device comprising an example thermal element coupled to an example catheter according to some embodiments.

Referring now to FIG. 4, some embodiments may include a catheter assembly 200 to passively open a fluid path. Some embodiments of the catheter assembly 200 may include a catheter adapter 202 having a proximal end 204, a distal end 206, and a lumen extending therebetween. In some embodiments, the catheter 102 may extend from the distal end 206 of the catheter adapter 202.

In some embodiments, the catheter 102 may include a proximal end 104, the tip 106, and a length of tubing 108 therebetween. In some embodiments, the length of tubing 108 may include one or more mechanical features to facilitate flexibility along the length of tubing 108. In some embodiments, the mechanical features may promote flexibility to create the bent portion 112 when the length of tubing 108 is disposed within the vasculature 122.

For example, as shown in FIG. 4, some embodiments of the catheter 102 may include a catheter 102 having an extended length 400 to allow the tip 106 to rest in a substantially centered position within the vasculature 122 during a dwell period. In some embodiments, the extended length 400 may facilitate passive lifting of the tip 106 of the catheter 102 within the vasculature 122. In some embodiments, the extended length 400 may facilitate passive repositioning of the tip 106 of the catheter 102 within the vasculature 122 to avoid an obstruction 202.

Referring now to FIG. 5, some embodiments of the catheter 102 may include one or more joints 500, hinges, bends, or other suitable mechanical junctures to create the bent portion 112 when the catheter 102 is disposed within the vasculature 122. In some embodiments, the one or more joints 500 may be coupled to or integrated with the length of tubing 108. Some embodiments of the joints 500 may be disposed proximate the tip 106 of the catheter 102 to facilitate movement of the tip 106 relative to the length of tubing 108. In other embodiments, the joints 500 may be disposed along the length of tubing 108. Some embodiments of the joints 500 may be bi-directional or multi-directional. In some embodiments, the one or more joints 500 may urge the tip 106 of the catheter 102 in a single direction.

Figure 6:
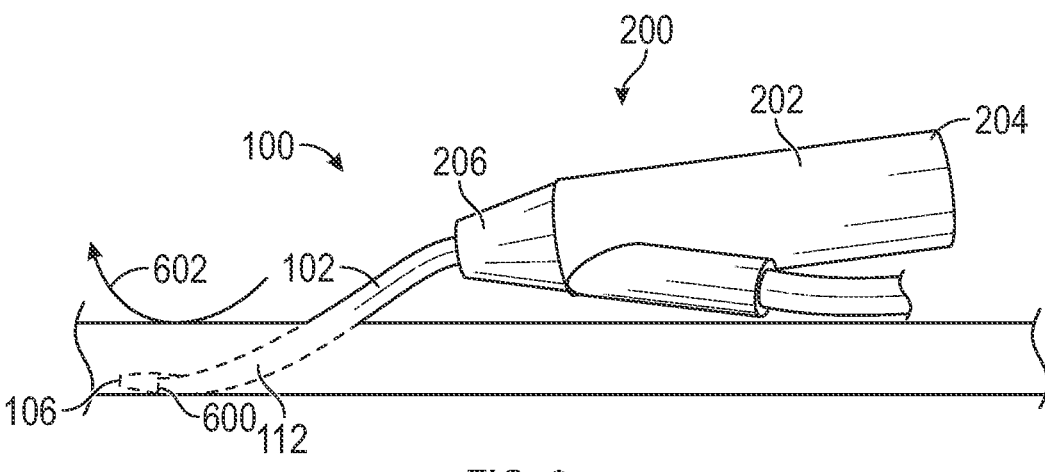
FIG. 6 is a side perspective view of an example vascular access device comprising a catheter having an extended length according to some embodiments.

Referring now to FIG. 6, in some embodiments, the catheter 102 may include one or more thermal elements 600 coupled to or integrated with the length of tubing 108. In some embodiments, the catheter 102 and the thermal element 600 may be monolithically formed as a single unit.

Some embodiments of the thermal element 600 may be located proximate the tip 106 to facilitate passively moving and/or re-directing the tip 106 with respect to the length of tubing 108, as indicated by arrow 602 in FIG. 6. For example, in some embodiments, the thermal element 600 may change shape in response to the temperature within the vasculature 122. In some embodiments, this shape change may cause the tip 106 of the catheter 102 to move relative to the length of tubing 108. Of course, in some embodiments, one or more of the thermal elements 600 may be disposed along the length of tubing 108 at any location intermediate to the tip 106 and the proximal end 104.

As discussed previously with reference to FIG. 2, some embodiments of a thermal element 600 may include a metal, plastic, or other suitable material having thermal properties that react to a change in temperature by changing shape. In some embodiments, the thermal element 600 may expand or contract in response to the temperature of the surrounding environment. For example, in some embodiments, the thermal element 600 may include nitinol, scandium trifluoride ($ScF_3$), or another suitable material.

Figure 7A:
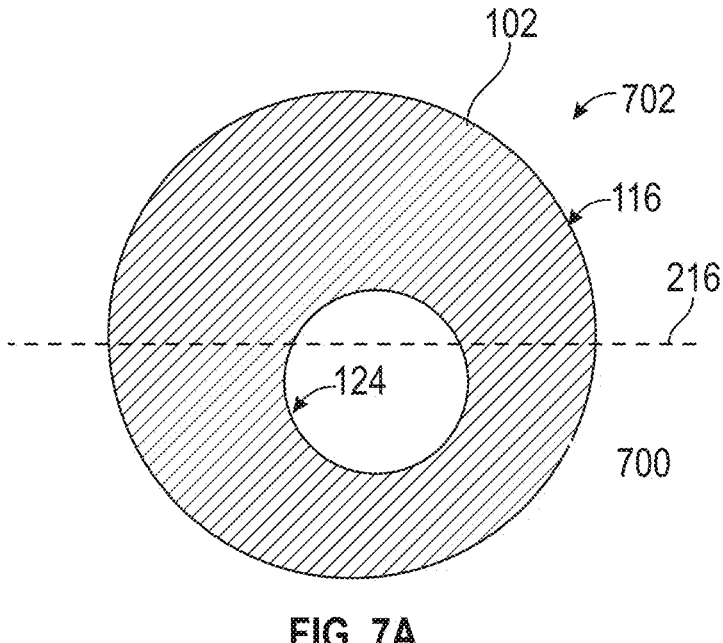
FIG. 7A is a cross-sectional view of an example catheter having an asymmetrical cross-section according to some embodiments.

Referring now to FIG. 7A, in some embodiments, the catheter 102 may include a catheter wall 700 having an asymmetrical cross-section 702 in which the center of the lumen 214 of the catheter 102 is offset from the centerline 216 of the catheter 102, and the sidewall of the catheter 102 varies around the circumference of the catheter 102, thereby resulting in the bent portion 112 along the length of tubing 108. In some embodiments, the bent portion 112 may result from the catheter 102 including the asymmetrical cross-section 702 in addition to one or more other mechanical features or thermal elements 600 coupled thereto or integrated therewith.

For example, in some embodiments, the catheter 102 may include the guidewire extending along the length of tubing

108. In some embodiments, the length of tubing 108 may include the asymmetrical 702 catheter wall 700 having the guidewire 110 embedded therein. In this manner, the resilient bent portion 112 may result from both the shape and orientation of the guidewire 110 as well as the asymmetrical cross-section 702 of the catheter wall 700.

Figure 7B:
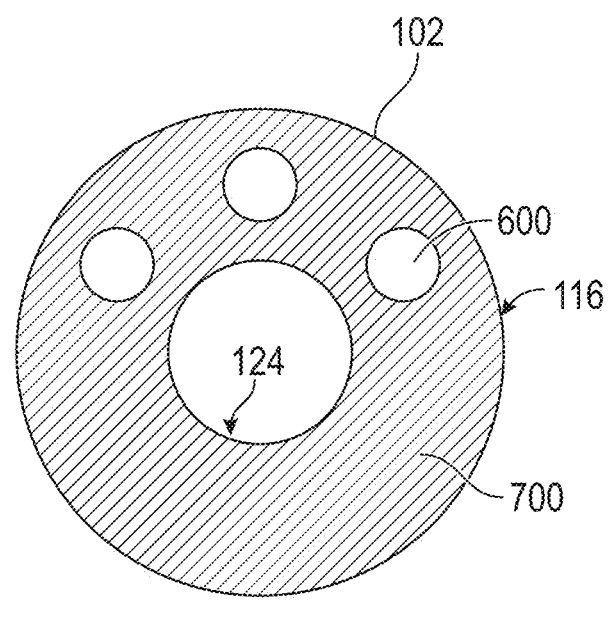
FIG. 7B is a cross-sectional view of an example catheter embedded with an example material having unique thermal properties according to some embodiments.
Figure 8:
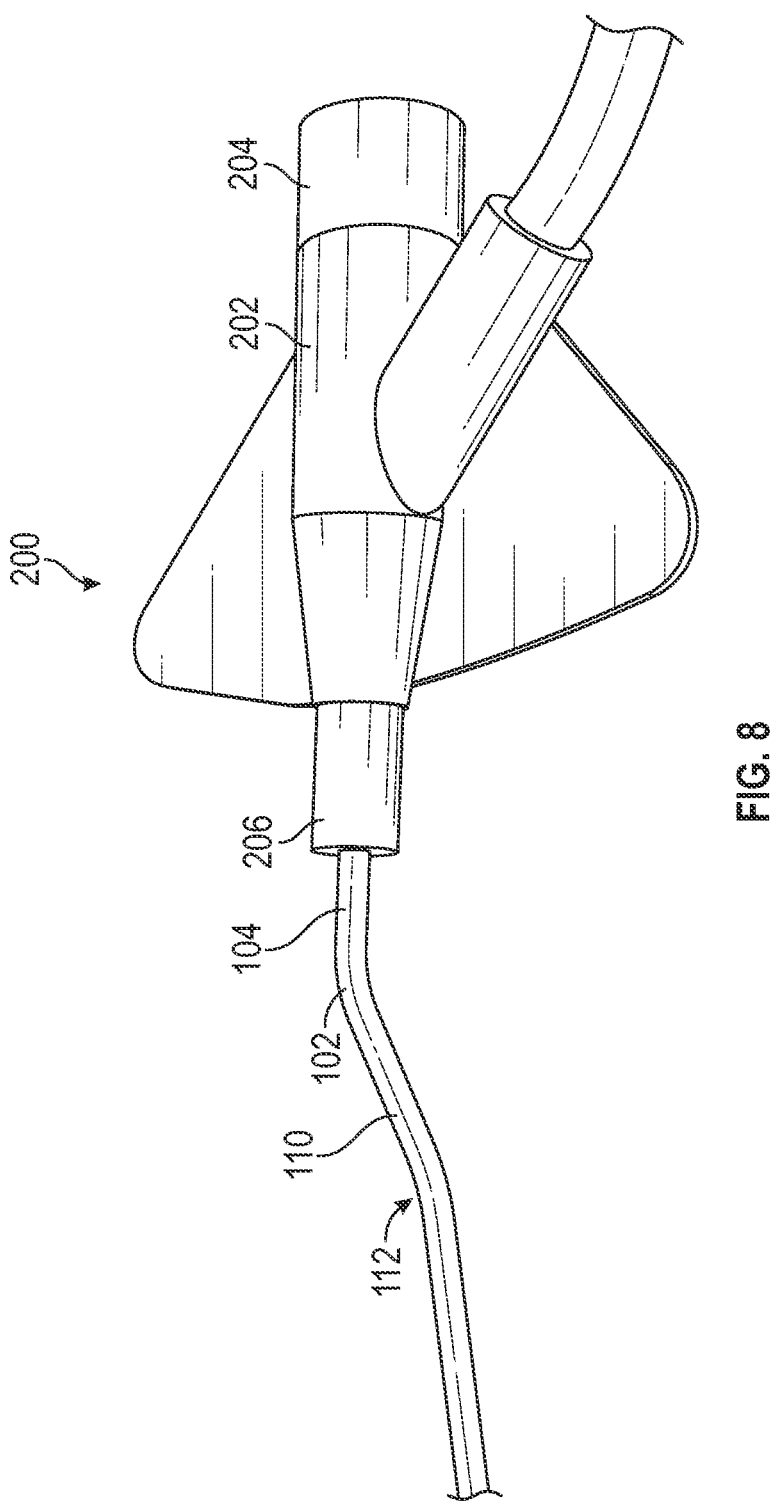
FIG. 8 is an upper perspective view of an example catheter adapter, illustrating an example guidewire extending along an example catheter according to some embodiments.

Referring now to FIG. 7B, in other embodiments, the catheter 102 may include one or more thermal elements 600 coupled to or embedded into the catheter wall 700. In some embodiments, the catheter wall 700 may be asymmetrical 702 to further support movement of the thermal elements 600 within the vasculature 122 to create the bent portion 112. In other embodiments, the catheter wall 700 may include a substantially symmetric cross-sectional profile.

As shown, in some embodiments, multiple thermal elements 600 may be embedded into or co-extruded with the catheter wall 700. In some embodiments, multiple thermal elements 600 may be coupled to the catheter wall 700. In some embodiments, the multiple thermal elements 600 may be evenly spaced around the catheter wall 700. In other embodiments, the multiple thermal elements 600 may be grouped together or otherwise located or oriented as desired to promote passive bending of the length of tubing 108 and/or creation of the bent portion 112.

Referring now to FIG. 1, in some embodiments, the vasculature 122 may include a longitudinal axis 120. Some embodiments of the bent portion 112 of the catheter 102 may direct the tip 106 of the catheter 102 upward within the vasculature 122 in a substantially transverse direction relative to the longitudinal axis 120. In some embodiments, the bent portion 112 may direct the tip 106 of the catheter 102 downward within the vasculature 122 in a substantially transverse direction relative to the longitudinal axis 120. In some embodiments, the bent portion 112 may direct the tip 106 of the catheter 102 laterally within the vasculature 122 relative to the longitudinal axis 120. In any case, the bent portion 112 may be substantially resilient and/or may be temperature-activated such that after the needle 210 has been withdrawn or otherwise removed, the tip 106 of the catheter 102 may be passively re-oriented within the vasculature 122 to clear a fluid path.

Referring now to FIGS. 9A-E, some embodiments of the resilient bent portion 112 may include an initial shape 900a, 900b, 900c, 900d, 900e. In some embodiments, the initial shape 900a, 900b, 900c, 900d, 900e may include a length of tubing 108 having a first portion 902 that is misaligned relative to a second portion 904 of the length of tubing 108, thereby forming the bent portion 112. In some embodiments, the second portion 904 may extend from the first portion 902. In some embodiments, the length of tubing 108 may further include a third portion 906 extending from the second portion 904. Some embodiments of the third portion 906 may be misaligned with respect to the second portion 904. In some embodiments, the third portion 906 may be aligned or substantially aligned with the first portion 902. In other embodiments, the third portion 906 may be misaligned with respect to the first portion 902. In some embodiments, a proximal portion may extend from a proximal end of the bent portion in a first direction, and a tip portion may extend from a distal end of the bent portion in a second direction after insertion into the vasculature, with the second direction being substantially opposite the first direction.

In any case, the resilient bent portion 112 may include an initial shape 900a, 900b, 900c, 900d, 900e configured to urge the tip 106 of the catheter 102 upward in a substantially transverse direction with respect to the longitudinal axis 120 of the vasculature 122. In some embodiments, the initial shape 900*a*, 900*b*, 900*c*, 900*d*, 900*e* may urge the tip 106 of the catheter 102 upward with respect to the first portion 902 and/or second portion 904 of the catheter 102. In this manner, some embodiments of the catheter 102 may enable the tip 106 of the catheter 102 to passively avoid interference with an obstruction 202 located or disposed within the vasculature 122.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A vascular access device comprising:
  a catheter comprising a proximal end, a tip, and a length of tubing therebetween; and
  a guidewire extending along the length of tubing, wherein the guidewire is embedded into at least a portion of the catheter, the guidewire comprising a bent portion, a proximal portion extending from a proximal end of the bent portion in a first direction, and a tip portion extending from a distal end of the bent portion in a second direction after insertion into the vasculature, wherein the second direction is substantially opposite the first direction, and after insertion into the vasculature, at least a portion of the length of tubing substantially conforms to a shape of the guidewire.

2. The vascular access device of claim 1, wherein the catheter comprises a lumen having a distal opening and providing a first fluid path, and at least one fenestration providing an additional fluid path.

3. The vascular access device of claim 1, wherein the guidewire comprises the bent portion before insertion into the vasculature.

4. The vascular access device of claim 3, wherein the guidewire comprises a metal, a metal alloy, polycarbonate, or plastic.

5. The vascular access device of claim 1, wherein the guidewire is configured to change shape after insertion into the vasculature to form the bent portion.

6. The vascular access device of claim 5, wherein the change in shape occurs passively.

7. The vascular access device of claim 5, wherein the guidewire comprises one of a shape memory alloy or a material that contracts with increasing temperature.

8. The vascular access device of claim 5, wherein the guidewire comprises one of nitinol and scandium trifluoride ($ScF_3$).

9. The vascular access device of claim 1, wherein the guidewire is positioned on or within a single portion of a circumference of the catheter.

10. The vascular access device of claim 1, wherein the proximal portion and the tip portion are misaligned.

11. The vascular access device of claim 1, wherein the proximal portion and the tip portion are aligned.

* * * * *